United States Patent [19]

Hoehn et al.

[11] 4,115,394

[45] Sep. 19, 1978

[54] AMINO DERIVATIVES OF 6-PHENYLPYRAZOLO[3,4-B]PYRIDINES

[75] Inventors: Hans Hoehn, Tegernheim; Ernst Schulze, Regensburg, both of Fed. Rep. of Germany

[73] Assignee: E. R. Squibb & Sons, Inc., Princeton, N.J.

[21] Appl. No.: 467,048

[22] Filed: May 6, 1974

[51] Int. Cl.$^2$ .................................... C07D 471/04
[52] U.S. Cl. .................... 260/296 H; 260/295 F; 424/256
[58] Field of Search .................. 260/295 F, 296 H

[56] References Cited

U.S. PATENT DOCUMENTS 3,542,793  11/1970  Rossi et al. .................. 260/296 H

OTHER PUBLICATIONS

Dorn et al., "Ber." V.101 pp. 3256–3277 (1968).

Primary Examiner—Natalie Trousof
Assistant Examiner—R. W. Ramsuer
Attorney, Agent, or Firm—Lawrence S. Levinson; Merle J. Smith

[57] ABSTRACT

New amino derivatives of 6-phenylpyrazolo[3,4-b]pyridines have the general formula

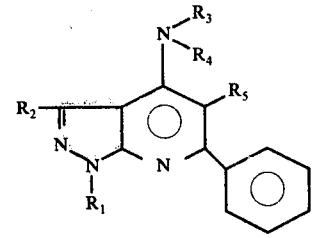

They are useful as anti-inflammatory and diuretic agents. In addition this type of compound increases the intra-cellular concentration of adenosine-3',5'-cyclic monophosphate.

8 Claims, No Drawings

AMINO DERIVATIVES OF 6-PHENYLPYRAZOLO[3,4-b]PYRIDINES

SUMMARY OF THE INVENTION

This invention relates to new amino derivatives of 6-phenylpyrazolo[3,4-b]pyridines. These new compounds have the general formula

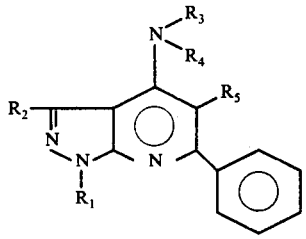
(I)

The symbols have the following meanings in formula I and throughout this specification.

$R_1$ is hydrogen, lower alkyl or phenyl-lower alkyl.
$R_2$ is hydrogen or lower alkyl.
The basic nitrogen group

in an acyclic amino group wherein $R_3$ and $R_4$ each is hydrogen, lower alkyl, phenyl, substituted phenyl, (wherein the substituent is lower alkyl, carboxy or $CF_3$) or phenyl-lower alkyl.
$R_5$ is hydrogen, lower alkyl, phenyl or phenyl-lower alkyl. The lower alkyl groups are straight or branched chain groups of up to seven carbon atoms.

Preferred are those compounds wherein $R_1$ is lower alkyl, especially methyl or ethyl, $R_2$ is hydrogen or methyl, $R_3$ and $R_4$ each is hydrogen or lower alkyl, especially wherein the lower alkyl has up to four carbon atoms, $R_5$ is preferably hydrogen.

DETAILED DESCRIPTION OF THE INVENTION

The new compounds of formula I are formed by the following series of reactions. The symbols in the structural formulas have the same meanings as previously described.

A 5-aminopyrazole of the formula

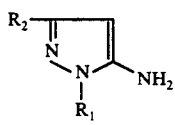
(II)

prepared according to the procedure described in Z. f. Chemie 10, 386–388 (1970) is made to react with a benzoyl acetic acid ester of the formula:

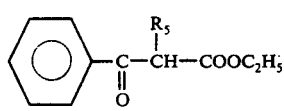
(III)

by heating at a temperature of about 140° C in the presence of polyphosphorus acid producing a compound of the formula

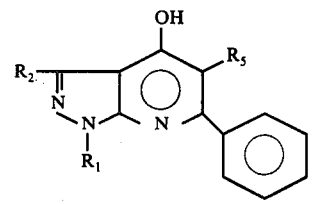
(IV)

Subsequently, this 4-hydroxy derivative is refluxed for several hours with a phosphorus halide like phosphorus oxychloride to obtain the intermediate of formula

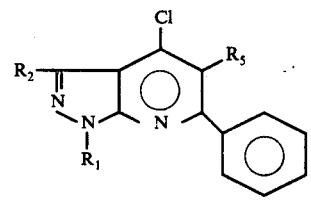
(V)

The products of formula I are then produced from the compounds of formula V with the appropriate amine of the formula

(VI)

This reaction is effected by treating the reactants in an autoclave at elevated temperatures.

According to a modification of the foregoing procedure, a product of formula I wherein $R_1$ is hydrogen, may be produced. By this modification a 5-aminopyrazole of formula II wherein $R_1$ is a heteromethyl group is used having the formula

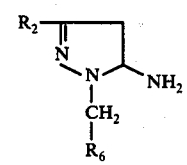
(IIa)

$R_6$ represents a heterocyclic nucleus like furyl, pyridyl, or the like. This material is processed as described above to get a compound of the formula

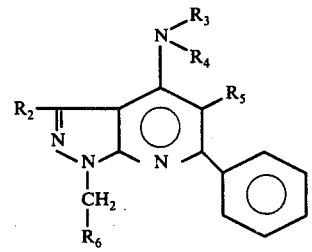
(Ia)

At this point, the compound of formula Ia is oxidized with an oxidizing agent like selenium dioxide in a high boiling solvent like diethyleneglycol dimethyl ether at about 160° C. This yields a compound of formula I wherein $R_1$ is hydrogen.

The compounds of formula I form salts which are also part of this invention. The salts include acid addition salts, particularly the non-toxic, physiologically acceptable members. The bases of formula I form salts by reaction with a variety of inorganic and organic acids providing acid addition salts including, for example, hydrohalides (especially hydrochloride and hydrobromide), sulfate, nitrate, borate, phosphate, oxalate, tartrate, malate, citrate, acetate, ascorbate, succinate, benzenesulfonate, mthanesulfonate, cyclohexanesulfamate and toluenesulfonate. The acid addition salts frequently provide a convenient means for isolating the product, e.g., by forming and precipitating the salt in an appropriate menstrum in which the salt is insoluble, then after separation of the salt, neutralizing with a base such as barium hydroxide or sodium hydroxide, to obtain the free base of formula I. Other salts may then be formed from the free base by reaction with an equivalent of acid.

The new compounds of this invention have antiinflammatory properties and are useful as antiinflammatory agents, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single or 2 to 4 divided doses, as indicated by the carageenan edema assay in rats. The active substance may be utilized in compositions such as tablets, capsules, solutions or suspensions containing up to about 200 mg per unit of dosage of a compound or mixture of compounds of formula I or a physiologically acceptable acid addition salt thereof. They may be compounded in conventional manner with a physiologically acceptable vehicle or carrier, excipient, binder preservative, stabilizer, flavor, etc. as called for by accepted pharmaceutical practice. Topical preparations containing about 0.01 to 3 percent by weight of active substance in a lotion, salve or cream may also be used.

The compounds of this invention also have diuretic activity and may be used for the relief of conditions characterized by a excessive accumulation of water such as the edemas associated with congestive heart failure, toxemia of pregnancy, tension and in the alleviation of salt retention caused by therapeutic agents. Representative dosages, which can be given in single or two to four divided doses, are in the range of 200 mg. to 3 g., preferably 500 to 1000 mg., per day which can be formulated in oral dosage forms described above.

The new compounds also increase the intracellular concentration of adenosine-3',5'-cyclic monophosphate, and thus by the administration of about 1 to 100 mg/kg/day, preferably about 10 to 50 mg/kg., in single or two to four divided doses in conventional oral or parenteral dosage forms such as those described above can be used to alleviate the symptoms of asthma.

The following examples are illustrative of the invention.

EXAMPLE 1

4-Dimethylamino-1,3-dimethyl-6-phenyl-1H-pyrazolo[3,4-b]-pyridine hydrochloride (a)

1,3-Dimethyl-4-hydroxy-6-phenyl-1H-pyrazolo[3,4-b]pyridine 96 gms. of benzoylacetic acid ethyl ester (0.5 mol.) are added dropwise to a stirred mixture of 55.5 gms. of 5-amino-1,3-dimethylpyrazole (0.5 mol) and 250 gms. of polyphosphorus acid heated to 120° C. After the reaction has occurred, which can be recognized by the changing of the color, the whole is heated for an additional hour at 120° C. After the mixture has cooled to room temperature, 600 ml. of water are added and stirring is continued until the compound becomes crystalline. The mixture is allowed to stand overnight and is then filtered off. The collected 1,3-dimethyl-4-hydroxy-6-phenyl-1H-pyrazolo[3,4-b]pyridine is washed with dilute ammonia, dried and treated with ethyl acetate yielding 73.6 gms. (61.6%), m.p. 262°–264°.

(b)

4-Chloro-1,3-dimethyl-6-phenyl-1H-pyrazolo[3,4-b]pyridine 73 gms. of 1,3-dimethyl-4-hydroxy-6-phenyl-1H-pyrazolo[3,4-b]pyridine (0.31 mol.) are refluxed in 800 ml. of phosphorus oxychloride for 6 hours. The excess phosphorus oxychloride is removed in vacuo and the oily residue is treated with ice-water by which operation the compound becomes solid. The compound is extracted with ether, washed with an aqueous sodium carbonate solution (10%) and again with water. Evaporation of the dried ($Na_2SO_4$) and charcoal treated ethereal extract provides 4-chloro-1,3-dimethyl-6-phenyl-1H-pyrazolo[3,4-b]-pyridine which is washed with absolute ethanol, yield: 55.6 gms. (69.8%) of white product melting at 89°–90° C.

(c)

4-Dimethylamino-1,3-dimethyl-6-phenyl-1H-pyrazolo[3,4-b]pyridine 15.5 gms. of 4-chloro-1,3-dimethyl-6-phenyl-1H-pyrazolo[3,4-b]pyridine (0.06 mol.) are added to 132 ml. of a solution of dimethylamine (40%). The reaction mixture is heated at 190°–200° C. for 16 hours in an autoclave and after cooling to room temperature is evaporated in vacuo. The residue is treated with water and extracted with ether. After evaporation of the extract, the 4-dimethylamino-1,3-dimethyl-6-phenyl-1H-pyrazolo[3,4-b]pyridine (15.6 gms. = 98%) is recrystallized from ligroin, m.p. 90°–91° C.

(d)

4-Dimethylamino-1,3-dimethyl-6-phenyl-1H-pyrazolo[3,4-b]pyridine hydrochloride

To 16.5 gms. of 4-dimethylamino-1,3-dimethyl-6-phenyl-1H-pyrazolo[3,4-b]pyridine (0.062 mol.) dissolved in 250 ml. of absolute ethanol, 10.7 ml. of ethereal hydrochloric acid (228 gms/1) are added. The solution is allowed to crystallize overnight to obtain 17.2 gms. (91%) of the hydrochloride, m.p. 219°–220° C. (dec.)

EXAMPLE 2

4-Amino-1,3-dimethyl-6-phenyl-1H-pyrazolo[3,4]pyridine hydrochloride 12.9 gms. of 4-chloro-1,3-dimethyl-6-phenyl-1H-pyrazolo[3,4-b]pyridine (0.05 mol.) are reacted with 100 ml. of alcoholic ammonia (105 mgs/1) and 100 ml. of concentrated aqueous ammonia at 190° C. for 12 hours in an autoclave. Then proceeding according to the procedure of Example 1 c yields 11.4 gms. (93%) of 4-amino-1,3-dimethyl-6-phenyl-1H-pyrazolo[3,4-b]pyridine, m.p. 175°-176° C. (ligroin).

The hydrochloride is prepared by dissolving 4-amino-1,3-dimethyl-6-phenyl-1H-pyrazolo[3,4-b]pyridine in absolute ethanol and adding ethereal hydrochloric acid, yield 96%, m.p. 293°-295° C.(dec.).

EXAMPLE 3

4-Butylamino-1-ethyl-6-phenyl-1H-pyrazolo[3,4-b]pyridine

(a)

1-Ethyl-4-hydroxy-6-phenyl-1H-pyrazolo[3,4-b]pyridine hydrochloride 116 gms. of benzoylacetic acid ethyl ester (0.6 mol.) are added dropwise over a period of 15-20 minutes to a stirred mixture of 66 gms. of 5-amino-1-ethylpyrazole (0.6 mol.) and 300 gms. of polyphosphorus acid heated to 140° C. The reaction temperature is maintained for two hours. After the mixture has cooled to room temperature, 850 ml. of water are added with stirring and the solution is neutralized by means of concentrated ammonia. The precipitated oily compound is repeatedly extracted with chloroform. After evaporation of the chloroform, the residual oily compound is dissolved in about 300 ml. of 2N aqueous sodium hydroxide and the solution is extracted with ether. Then the aqueous alkaline solution is treated with charcoal, filtered and acidified with dilute acetic acid. The precipitated oily compound is again extracted with ether and after the extract is dried (Na$_2$SO$_4$) the hydrochloride salt is formed by addition of ethereal hydrochloride acid to the ethereal solution. The oily precipitate soon becomes crystalline. The filtered product is treated with about 200 ml. of acetone and again filtered off yielding 99.1 gms. (60%). The 1-ethyl-4-hydroxy-6-phenyl-1H-pyrazolo[3,4-b]pyridine hydrochloride (m.p. 220°-232° C.) is recrystallized from absolute ethanol, m.p. 251°-253° C.

(b)

4-Chloro-1-ethyl-6-phenyl-1H-pyrazolo[3,4-b]pyridine

A mixture of 193.9 gms. of 1-ethyl-4-hydroxy-6-phenyl-1H-pyrazolo[3,4-b]pyridine (0.7 mol.) and 1000 ml. of phosphorus oxychloride is refluxed for 5 hours. The excess phosphorus oxychloride is removed in vacuo and the residue is treated with ice water. The mixture is then extracted three times with ether, the ether layer is separated, dried over sodium sulfate, treated with charcoal and concentrated in vacuo. The residue solidifies on cooling (142.4 gms = 79%; m.p. 43°-45° C.) and the product, 4-chloro-1-ethyl-6-phenyl-1H-pyrazolo[3,4-b]pyridine is recrystallized from hexane, m.p. 46°-48° C.

(c)

4-Butylamino-1-ethyl-6-phenyl-1H-pyrazolo[3,4-b]pyridine 15.5 gms. of 4-chloro-1-ethyl-6-phenyl-1H-pyrazolo[3,4-b]pyridine (0.06 mol.) are reacted with 100 ml. n-butylamine at 190°-200° C. in an autoclave for 7 hours. The reaction mixture is then evaporated to dryness in vacuo and the residue is treated with 150 ml. of water. The sticky crystalline compound is extracted with ether. The ethereal solution is treated with charcoal, filtered, dried over sodium sulfate and concentrated in vacuo. The residual compound is recrystallized from cyclohexane. The yield of 4-butylamino-1-ethyl-6-phenyl-1H-pyrazolo[3,4-b]pyridine is 14.5 gms. (82.3%), m.p. 95°-96° C.

The hydrochloric acid salt is formed by dissolving 4-butylamino-1-ethyl-6-phenyl-1H-pyrazolo[3,4-b]pyridine in acetonitrile and adding ethereal hydrochloric acid. Evaporation of the solution in vacuo provides the hydrochloride, m.p. 139°-143° C. (dec.).

EXAMPLE 4

4-Butylamino-1-ethyl-3-methyl-6-phenyl-1H-pyrazolo[3,4-b]pyridine hydrochloride

(a)

1-Ethyl-4-hydroxy-3-methyl-6-phenyl-1H-pyrazolo[3,4-b]pyridine

Treatment of 5-amino-1-ethyl-3-methylpyrazole with benzoyl acetic acid ethyl ester is polyphosphorus acid according to the procedure of Example 1 a (reaction temperature 130° C), yields 1-ethyl-4-hydroxy-3-methyl-6-phenyl-1H-pyrazole[3,4-b]-pyridine, yield 64.7%, m.p. 253°-254° C. (absolute ethanol).

(b)

4-Chloro-1-ethyl-3-methyl-6-phenyl-1H-pyrazolo[3,4-b]pyridine

By treating the product of Example 4 a with phosphorus oxychloride according to the procedure of Example 1 b, 4-chloro-1-ethyl-3-methyl-6-phenyl-1H-pyrazolo[3,4-b]pyridine is obtained, yield 96%, m.p. 101°-103° C. (absolute ethanol).

(c)

4-Butylamino-1-ethyl-3-methyl-6-phenyl-1H-pyrazolo[3,4-b]-pyridine hydrochloride By treating the product of Example 4 b with butylamine as in Example 1 c and 1 d, 4-butylamino-1-ethyl-3-methyl-6-phenyl-1H-pyrazolo[3,4-b]pyridine (yield 96%, m.p. 146°-147° C.) and then its hydrochloride (yield 81%; m.p. 206°-208° C) are obtained.

EXAMPLE 5

4-Dimethylamino-6-phenyl-1H-pyrazolo[3,4-b]pyridine

(a)

4-Dimethylamino-1-(2-furyl)methyl-6-phenyl-1H-pyrazolo[3,4-b]pyridine 0.5 mol. of 1-(2-furyl)methyl-5-aminopyrazole is substituted for the 5-amino-1,3-dimethylpyrazole in part a of Example 1 and the procedure of that example is followed through part c to obtain 4-dimethylamino-1-(2-furyl)methyl-6-phenyl-1H-pyrazolo[3,4-b]pyridine.

(b)
4-Dimethylamino-6-phenyl-1H-pyrazolo[3,4-b]pyridine

0.1 mol of the product of part a and 0.18 mol. of selenium dioxide are suspended in 100 ml. of diethyleneglycol dimethyl ether. The mixture is heated with stirring at 160° C. and a few drops of water are added. This temperature is maintained for 1.5 hours. After cooling the mixture is neutralized with a dilute solution of aqueous ammonia to obtain the product 4-dimethylamino-6-phenyl-1H-pyrazolo[3,4-b]pyridine.

The following additional compounds are produced by the procedure of the Example indicated:

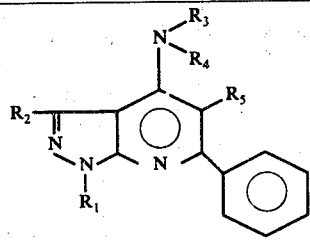

| Ex. | $R_1$ | $R_2$ | $R_3$ | $R_4$ | $R_5$ | Salt | m.p. | Yield | Produced according to example |
|---|---|---|---|---|---|---|---|---|---|
| 6 | —$C_2H_5$ | H | —CH($CH_3$)—$CH_2$—$CH_3$ | H | H | — | 105–106 | 61% | 3c |
| 7 | —$C_2H_5$ | H | —CH($CH_3$)—$CH_2$—$CH_3$ | H | H | HCl | 151–153 | 89% | 3c |
| 8 | —$C_2H_5$ | —$CH_3$ | —CH($CH_3$)—$CH_2$—$CH_3$ | H | H | — | oil | 100% | 1c |
| 9 | —$C_2H_5$ | —$CH_3$ | —CH($CH_3$)—$CH_2$—$CH_3$ | H | H | HCl | 198–200 | 76% | 1d |
| 10 | —$CH_3$ | —$CH_3$ | —$CH_2$—CH($CH_3$)$_2$ | H | H | — | 86–87 | 97% | 1c |
| 11 | —$CH_3$ | —$CH_3$ | —$CH_2$—CH($CH_3$)$_2$ | H | H | HCl | 220–222 | 60% | 1d |
| 12 | —$CH_3$ | —$CH_3$ | —CH($CH_3$)—$CH_2$—$CH_3$ | H | H | — | 93–94 | 100% | 1c |
| 13 | —$CH_3$ | —$CH_3$ | —CH($CH_3$)—$CH_2$—$CH_3$ | H | H | HCl | 196–199 | 76% | 1d |
| 14 | —$C_2H_5$ | —$CH_3$ | —CH($CH_3$)$_2$ | H | H | — | 153–154 | 70% | 2 |
| 15 | —$C_2H_5$ | —$CH_3$ | —CH($CH_3$)$_2$ | H | H | HCl | 257–260 | 96% | 2 |
| 16 | —$C_2H_5$ | H | —$CH_3$ | H | H | — | oil | — | 2 |
| 17 | —$C_2H_5$ | H | —$CH_3$ | H | H | HCl | 238–240 | 78% | 2 |
| 18 | —$C_2H_5$ | H | —$CH_2$—$CH_3$ | —$CH_2$—$CH_3$ | H | — | oil | 90% | 3 |
| 19 | —$C_2H_5$ | H | —$CH_2$—$CH_3$ | —$CH_2$—$CH_3$ | H | HCl | 184–186 | 73% | 3 |
| 20 | —⟨Ph⟩ | H | —$(CH_2)_2CH_3$ | H | —$CH_2CH_3$ | | | | 1 |
| 21 | $C_2H_5$ —$CH_2$— | H | —CH($CH_3$)$_2$ | H | —$CH_2CH_2CH_3$ | | | | 1 |
| 22 | —⟨Ph⟩—$CH_2CH_2$— | —$CH_3$ | —$CH_3$ | $CH_3$ | H | | | | 1 |
| 23 | —$C_2H_5$ | —$CH_2CH_3$ | —$CH_3$ | H | H | | | | 1 |
| 24 | H | H | H | H | —$CH_3$ | | | | 5 |
| 25 | —$C_2H_5$ | H | —⟨Ph⟩ | —⟨Ph⟩ | H | | | | 1 |
| 26 | H | H | —$CH_2$—⟨Ph⟩ | H | H | | | | 5 |
| 27 | —$C_2H_5$ | H | —$CH_2CH_2$—⟨Ph⟩ | H | H | | | | 1 |
| 28 | —$CH_3$ | —$CH_3$ | —$CH_2CH_2$—⟨Ph⟩ | H | —$CH_3$ | | | | 1 |
| 29 | —$C_2H_5$ | H | —⟨Ph-$CF_3$⟩ | H | H | | | | 1 |
| 30 | —$C_2H_5$ | H | —⟨Ph($CH_3$)$_2$⟩ | H | —$CH_3$ | | | | 1 |
| 31 | —$C_2H_5$ | H | —⟨Ph-COOH⟩ | H | H | | | | 1 |
| 32 | H | H | H | $CH_3$ | —⟨Ph⟩ | | | | 5 |
| 33 | —$CH_3$ | —$CH_3$ | —$(CH)_3CH_3$ | H | —$CH_2$—⟨Ph⟩ | | | | 1 |
| 34 | —$C_2H_5$ | H | —$CH_2CH_2$—⟨Ph⟩ | H | —$CH_2CH_2$—⟨Ph⟩ | | | | 1 |

-continued

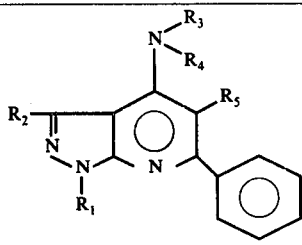

| Ex. | $R_1$ | $R_2$ | $R_3$ | $R_4$ | $R_5$ | Salt | m.p. | Yield | Produced according to example |
|---|---|---|---|---|---|---|---|---|---|
| 35 | —$C_2H_5$ | —$CH_3$ | —$CH_3$ | H | —C₆H₁₁ | | | | 1 |
| 36 | H | —$CH_2CH_3$ | —$CH_2CH_2CH_2CH_3$ | H | H | | | | 5 |
| 37 | H | H | —$CH_2CH_2CH_2CH_3$ | H | H | | | | 5 |

What is claimed is:

1. A compound having the formula

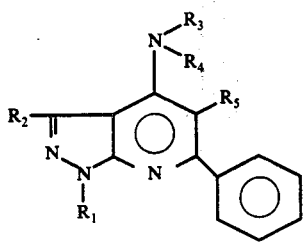

wherein $R_1$, $R_2$, $R_3$ and $R_4$ each is lower alkyl and $R_5$ is hydrogen.

2. A compound having the formula

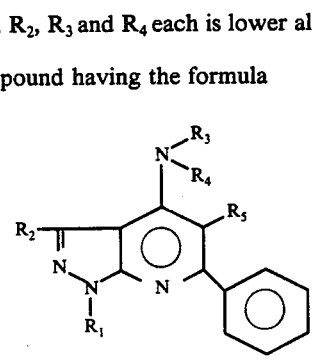

wherein $R_1$ and $R_3$ each is lower alkyl and $R_2$, $R_4$ and $R_5$ each is hydrogen.

3. A compound having the formula

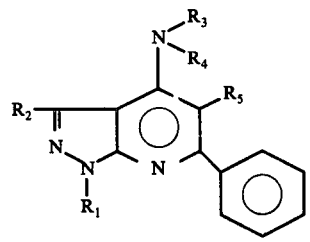

wherein $R_1$, $R_2$ and $R_3$ each is lower alkyl and $R_4$ and $R_5$ each is hydrogen.

4. A compound as in claim 1 wherein each lower alkyl group is methyl.

5. A compound having the formula

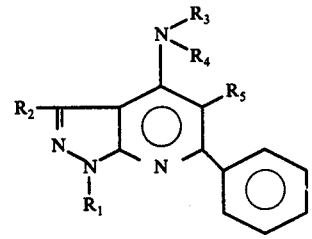

wherein $R_1$ and $R_2$ each is methyl and $R_3$, $R_4$ and $R_5$ each is hydrogen.

6. A compound as in claim 2 wherein $R_1$ is ethyl and $R_3$ is butyl.

7. A compound as in claim 3 wherein $R_1$ is ethyl, $R_2$ is methyl and $R_3$ is butyl.

8. A compound having the formula

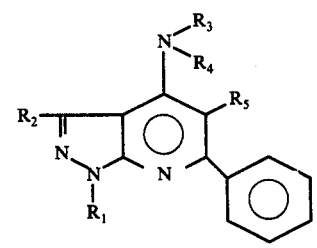

wherein $R_1$, $R_2$, $R_4$ and $R_5$ each is hydrogen and $R_3$ is butyl.

* * * * *